(12) United States Patent
Müller

(10) Patent No.: US 8,452,361 B2
(45) Date of Patent: May 28, 2013

(54) OCULAR SENSOR FOR THE DETECTION OF AN ANALYTE IN EYE WATER

(75) Inventor: Achim Müller, Grossostheim (DE)

(73) Assignee: Eyesense AG, Basel (CH)

(*) Notice: Subject to any disclaimer, the term of this patent is extended or adjusted under 35 U.S.C. 154(b) by 563 days.

(21) Appl. No.: 12/523,434

(22) PCT Filed: Jan. 14, 2008

(86) PCT No.: PCT/EP2008/050347
§ 371 (c)(1),
(2), (4) Date: Jun. 8, 2010

(87) PCT Pub. No.: WO2008/087118
PCT Pub. Date: Jul. 24, 2008

(65) Prior Publication Data
US 2010/0249548 A1    Sep. 30, 2010

(30) Foreign Application Priority Data
Jan. 17, 2007   (DE) .................. 10 2007 003 341

(51) Int. Cl.
*A61B 1/00* (2006.01)
*A61B 5/05* (2006.01)
(52) U.S. Cl.
USPC ........................................ 600/318; 600/356
(58) Field of Classification Search
USPC ............... 600/318–321, 326, 327, 329, 347, 600/398, 399, 345, 356, 365
See application file for complete search history.

(56) References Cited

U.S. PATENT DOCUMENTS

| 6,312,393 | B1 | 11/2001 | Abreu |
| 6,579,690 | B1 | 6/2003 | Bonnecaze et al. |
| 2002/0099359 | A1 | 7/2002 | Santini, Jr. et al. |
| 2004/0054385 | A1 | 3/2004 | Lesho |
| 2005/0154271 | A1* | 7/2005 | Rasdal et al. .................. 600/347 |
| 2006/0155179 | A1* | 7/2006 | Muller et al. .................. 600/318 |

FOREIGN PATENT DOCUMENTS

| AU | 2004201752 B2 | 5/2004 |
| JP | 51-075498 | 5/1976 |
| JP | 05-093723 | 4/1993 |
| JP | 08-238221 | 9/1996 |
| JP | 2000-338260 | 12/2000 |

(Continued)

OTHER PUBLICATIONS

International Preliminary Report on Patentability for PCT/EP2008/050347 (Translation), mail date of Sep. 3, 2009.

*Primary Examiner* — Clayton E LaBalle
*Assistant Examiner* — Minh Phan
(74) *Attorney, Agent, or Firm* — Fanelli Haag & Kilger PLLC

(57) ABSTRACT

An ocular sensor (110) is proposed for verification of at least one analyte in an eye fluid. The ocular sensor (110) is composed of at least one sensor material which is designed to change at least one optical characteristic in the presence of the at least one analyte. Furthermore, the ocular sensor (110) comprises at least one sensor chip which has at least one integrated optical detector (122) for verification of the optical characteristic. A measurement system (166) is also proposed for verification of at least one analyte in an eye fluid, which measurement system (166) comprises an ocular sensor (110) according to the invention as well as an evaluation unit (168) which is designed to interchange information with the sensor chip (118).

32 Claims, 3 Drawing Sheets

FOREIGN PATENT DOCUMENTS

| | | |
|---|---|---|
| JP | 2000-517231 | 12/2000 |
| JP | 2002-523774 | 7/2002 |
| JP | 2002-528212 | 9/2002 |
| JP | 2002-536103 | 10/2002 |
| JP | 2003-507717 | 2/2003 |
| JP | 2003-520091 | 7/2003 |
| JP | 2004-502252 | 1/2004 |
| WO | WO 01/13783 A1 | 3/2001 |
| WO | WO 02/087429 A1 | 11/2002 |
| WO | WO 2004/071287 A1 | 8/2004 |
| WO | WO 2005/015237 A1 | 2/2005 |

\* cited by examiner

OCULAR SENSOR FOR THE DETECTION OF AN ANALYTE IN EYE WATER

FIELD OF THE INVENTION

The invention relates to an ocular sensor for verification of at least one analyte in an eye fluid, for example in tear fluid, interstitial eye fluid or aqueous humour. The invention also relates to a measurement system for verification of an analyte in an eye fluid. Ocular sensors and measurement systems such as these are used in particular for medical diagnosis, for example for verification and/or for quantitative measurement of a glucose concentration. However, other applications or analytes are also feasible.

PRIOR ART

The determination of the blood glucose concentration and appropriate medication are an essential component of daily life for diabetics. In this case, the blood glucose concentration must be determined quickly and easily several times a day, for example 2 to 7 times a day, in order to make it possible to take appropriate medical measures where necessary, for example to inject an appropriate dose of insulin. In addition to manual injection, medication is also provided in many cases by means of automatic systems, in particular using insulin pumps.

Conventional systems for determination of the blood glucose concentration are generally based on the patient or doctor perforating a skin area, for example by means of a suitable lancet system, and thus generating a blood sample. This sample is then analysed by means of suitable measurement methods, for example optical and/or electrochemical measurement methods, for its blood glucose content. In addition to verification using blood, verification can also be achieved using other bodily fluids, for example using urine.

In order to reduce the unpleasant aspects for the patient associated with the frequent generation of blood samples, various non-invasive or minimal-invasive technologies have been developed for measurement of blood glucose concentrations. One technology is based on the measurement of glucose in eye fluids, for example tear fluid, aqueous humour or interstitial fluid. By way of example, WO 01/13783 describes an ocular sensor for glucose, which is in the form of an eye lens. The ocular sensor comprises a glucose receptor which is marked with a first fluorescence label, and a glucose competitor, which is marked with the second fluorescence label ("Donor").

The two fluorescence labels are chosen such that, when the competitor is bound to the receptor, the fluorescence of the second fluorescence label is quenched by a resonant fluorescence energy transfer. The proportion of the fluorescence-marked competitor which has been displaced by the glucose can be measured by monitoring the change in the fluorescence intensity at a wavelength around the fluorescence maximum of the quenchable fluorescence label. In this way, the glucose concentration in the eye fluid can be determined. This measurement can in turn be used to deduce the blood glucose concentration from it. Other types of verification are also feasible and will be familiar to a person skilled in the art, for example fluorescence verification of the first fluorescence label.

WO 02/087429 also describes a fluorescence photometer, by means of which blood glucose concentrations can be determined by measuring the glucose concentration in an eye fluid. The described apparatus is able to measure two fluorescence intensities at two different wavelengths at the same time.

The measurement of glucose or other analytes in eye fluids is normally limited by various factors. For example, one factor is that the eye fluids are normally available only in small amounts (for example tear fluids or interstitial fluids) or can be accessed only with difficulty (vitreous humour fluid or aqueous humour). The option of collecting these eye fluids as a sample therefore generally represents a very difficult procedure. In order to overcome or to reduce this restriction or difficulty, various options have been developed for in-vivo measurement. The already cited WO 01/13783 discloses one such in-vivo measurement system.

In the case of in-vivo diagnosis, the measurement signal frequently depends not only on the analyte concentration but also on the relative position of the instrument with respect to the measurement location. On the other hand, mechanically permanent fixing of the instrument to the patient is not possible, and in many cases is also not desirable. In order to achieve good positioning accuracy, simple mechanical spacers would have to be set to the individual requirements, and are therefore not suitable for mass production.

A further problem of many spectroscopic in-vivo measurement systems is the comparatively poor spectroscopic contrast between the measurement signal and the background. In many cases, this requires complex calibration, which frequently depends on the exact position, since the spectral background depends on the exact positioning (for example because of the different scattering behaviour of different tissue types and blood vessel types, the fluctuating tissue thickness and the tissue density, etc.). Measurement systems such as these therefore require reproducibly accurate positioning of the measurement system.

WO 2004/071287 discloses a fluorescence photometer which operates by means of two different beams and allows correct positioning of the instrument in front of the eye. A first fluorescence of the pupil is excited by means of a pilot beam, from which first fluorescence a distance is determined between the fluorescence photometer and the eye. When a correct distance is set, a measurement beam is automatically started, which excites a second fluorescence of the analyte sensor in the eye, from which the analyte concentration can in turn be determined. Despite the considerable measurement complexity with which the system disclosed in WO 2004/071287 is associated, it has been found that the measurement results of the analyte concentration may be subject to fluctuations, as before. Furthermore, in many cases, positioning processes carried out autonomously by the patient are required which in fact can be carried out only with difficulty by elderly patients or children and which therefore should ideally be avoided.

OBJECT OF THE INVENTION

The object of the invention is therefore to provide an ocular sensor and a measurement system which avoid the disadvantages and difficulties of the prior art described above and provide a simple and reliable capability for determination of the analyte concentration in an eye fluid and/or in some other bodily fluid, in particular in blood.

DESCRIPTION

This object is achieved by an ocular sensor according to claim 1 and by a measurement system according to claim 21. Advantageous developments of the invention are described in the dependent claims, which can be implemented both individually and in combination with one another.

An ocular sensor is proposed for verification of at least one analyte in an eye fluid. This ocular sensor is in this case designed such that it can be brought into contact with the eye fluid, this ocular sensor being designed appropriately for this purpose and produced using suitable materials. It is particularly preferable for the ocular sensor to comprise an eye lens (in particular a neutral or corrective contact lens). Alternatively or additionally, the ocular sensor may also comprise an eye implant and/or an inlay (for example for accommodation in the lower conjunctival sac). In both preferred cases, materials are preferably used which are bio-compatible, that is to say which are not toxic and which do not dissolve, are themselves not damaged or release toxic substances when used in the eye or when implanted in the eye. With regard to the configuration of an eye lens, reference may be made, for example, to WO 01/13783. With regard to analytes to be verified, reference can also be made, for example, to the disclosure in this document.

The ocular sensor according to the invention has at least one sensor material which is designed to change at least one optical characteristic in the presence of the at least one analyte to be verified. By way of example, this at least one optical characteristic may be a colour which changes in a corresponding manner in the presence of the analyte. However, it is particularly preferable for the at least one optical characteristic to be luminescence which can be excited by excitation light, in particular fluorescence and/or phosphorescence.

By way of example, the sensor material may contain a material which can bind the analyte to be verified and which changes its fluorescence characteristics (for example excitation capability, spectral characteristics or the like) when binding the analyte. Alternatively or additionally, a spectral characteristic of the analyte itself could also be verified, which changes when being bound to the receptor unit, for example as a result of quenching. Once again alternatively or additionally, a spectral characteristic of a further molecule could also be verified, for example of a competitor molecule which is bound to the receptor unit of the sensor material, is displaced therefrom in the presence of the analyte to be verified, and in this case once again changes its optical characteristics. To this extent, the expression optical characteristic may relate to the sensor material itself (for example a receptor and/or a competitor molecule) and/or to the analyte itself, or else a combination of these substances. Various types of sensor materials and verification principles such as these are described, for example, in WO 01/13783 A1, in WO 02/087429 A1, or in WO 2004/071287 A1. The material examples quoted there may also be referred to by way of example for the sensor material. This measurement principle can be used both for qualitative verification and for quantitative analysis.

To this extent, the proposed ocular sensor may correspond essentially to the ocular sensors known from the prior art. In contrast to the prior art, however, the ocular sensor according to the invention is also provided with at least one sensor chip. In particular, this sensor chip may be an application-specific integrated circuit (ASIC), or the sensor chip may have such an ASIC. Other types of sensor chip are also feasible, for example conventional ICs, and/or the combined use of a plurality of sensor chips. The use of alternative chip technologies is also feasible, for example the use of organic electronics, for example the use of organic transistors (for example polymer transistors) and/or hybrid technologies of organic and inorganic materials. ASICs may, however, preferably be produced on the basis of silicon chips or other semiconductor materials. Modern manufacturing methods make it possible to produce thin sensor chips, for example sensor chips with a thickness of 200 to 400 µm, for example 250 µm, and with lateral dimensions in the region of a few mm. Chips such as these can therefore be implanted without any problems in a human eye, for example in conjunctival tissue, and/or can be accommodated in an eye lens.

According to the invention, the sensor chip has at least one integrated optical detector for verification of the optical characteristic of the sensor material. For example, the optical detector may comprise one or more photodiodes which can detect luminescence light from the at least one sensor material and/or from the at least one analyte to be verified. Other types of detector may, however, also be used, for example different types of light-sensitive detectors without a diode characteristic.

In contrast to the ocular sensors which are known from the prior art, at least a portion of the measurement apparatus has therefore, according to the invention, been moved to the immediate vicinity of the location where the optical signal is created (that is to say the location at which the optical characteristic of the sensor material changes). The integration of the optical detector directly in the ocular sensor therefore ensures that there is always a constant distance between the sensor material and the optical detector. There is therefore no need for complex positioning measures for the optical detector. This considerably simplifies the handling of the ocular sensor, and this represents a considerable advantage in particular for elderly people, children and physically handicapped patients.

In this case, it is particularly preferable for the ocular sensor to have a carrier material in which the sensor chip is embedded. For example, by an appropriate geometry and/or choice of material, the carrier material can ensure bio-compatibility of the ocular sensor, that is to say for example an implantation capability and/or use in an eye lens or as an eye lens. At the same time, the carrier material may have the required mechanical characteristics, for example deformability and/or flexibility, a geometry as required for an eye lens or an implant, or the like.

In this case, the sensor material may be applied to the sensor chip. However, it is particularly preferable for the sensor material to be contained entirely or partially in the carrier material. For example, the sensor material may be mixed into the carrier material, dissolved in it or may be entirely or partially a component of this carrier material (for example in the form of functional groups which are bound to a matrix material of the carrier material). An implementation in microcapsules is also feasible, which can then in turn, for example, be dispersed into the carrier material. Combinations of the said techniques are also feasible.

In this case, the carrier material should comprise a material which is at least partially permeable for the analyte, for example a porous material, or a material which has a high diffusion coefficient for the analyte to be verified. In particular, it should be ensured that an adequate amount of the analyte can come into contact with the sensor material. It is particularly preferable to use a hydrogel. In this case, it is preferable, particularly for use in an eye lens and/or in an implant, for the carrier material to have deformable, in particular flexible, characteristics. At least partial optical transparency is also desirable, particularly when external excitation light, for example daylight, is used for the analyte verification (see below).

The advantages described above can be achieved by the integration of the optical detector for verification of the at least one optical characteristic or characteristic change as a result of the presence of the analyte to be verified. In further advantageous refinements of the invention, sensor materials are used, in particular, which, as described above, change a luminescence characteristic as a function of the presence of the at least one analyte.

In particular, this luminescence may be (in addition to or as an alternative to characteristics such as colour, refractive index, etc.) in particular luminescence which can be excited by excitation light, for example fluorescence or phosphorescence. The change in the optical characteristic depending on the presence of the analyte may then, for example, comprise an increase in the fluorescence as the analyte concentration rises. This will be the case, for example, when fluorescence of an analyte-receptor compound and/or fluorescence of a released competitor module, which is displaced by the analyte, is intended to be verified. Alternatively or additionally, the change may also comprise a decrease in the fluorescence as the analyte concentration rises. The latter would occur, for example, in the case in which fluorescence quenching of a receptor occurs in the presence of the analyte, and/or in the case of verification of the fluorescence of a receptor-competitor molecule compound, with the competitor molecule being displaceable by the analyte. Various other combinations and alternatives for the measurement of analyte-sensitive optical characteristics are feasible.

In the case of fluorescence and/or phosphorescence verification, one or more excitation light sources for the production of the excitation light can also be integrated onto the sensor chip, for example in the form of one or more light-emitting diodes and/or laser diodes. In the same way as the at least one optical detector, this excitation light source may be reduced, for example, by means of known techniques, and can preferably be integrated in an ASIC. However, in addition to the use of conventional inorganic semiconductor techniques, it is also possible to use other techniques, for example techniques which make use of organic semiconductor technology and, for example, comprise organic integrated circuits and/or organic light-emitting diodes and/or organic photodetectors.

The ocular sensor is in this case designed such that it allows the sensor material to be excited by the excitation light source. In addition to the option mentioned above for integration of the excitation light source, it is, however, also possible to use external light sources as the excitation light. Because of its availability, daylight in particular can be used as excitation light. This option can be implemented particularly easily, since daylight has a wide spectrum and since there is therefore no need for an internal power supply for the excitation light source. However, the term daylight should in this case be interpreted widely, and is intended to cover not only natural daylight but also environmental light of any type, for example also light from one or more artificial light sources. This allows use at different times of the day and in changing environmental conditions.

In both cases, that is to say in the case of integrated production of the excitation light and when using an external excitation light source, for example daylight, this preferably prevents the excitation light from entering the optical detector for verification of the at least one optical characteristic. For this purpose, in particular, the ocular sensor may have an optical background filter, in particular an optical bandpass filter or edge filter, which is designed and arranged to entirely or partially suppress an intensity of the excitation light. This therefore makes it possible to greatly reduce the background signal which the optical detector produces and which is caused by the excitation light and not by the change in the optical characteristic of the sensor material. Furthermore, the background filter can also select (transmit) a predetermined spectral range from the available excitation light, which is then used as suitable excitation light to excite the sensor material and/or a reference material.

Various filter techniques are known to those skilled in the art. For example, absorptive filter techniques can be used, for example simple colour filters. Alternatively or additionally, however, it is also possible to use more complex filter techniques, for example to use interference filters.

In this case, the background filter may be in the form of a separate background filter, for example in the form of a filter element arranged on the sensor chip or in the form of a filter element which is likewise embedded in the carrier material. Alternatively or additionally, the background filter may, however, also be entirely or partially in the form of a component of the carrier material, for example by mixing a dye which acts as an absorption filter into the carrier material, or dissolving such a dye therein. Once again, however, a direct chemical implementation in the carrier material is also possible, for example in the form of appropriate functional groups in the carrier material.

As a further (alternative or additional) measure to improve the signal quality of the ocular sensor, a sensor filter may be provided which is designed specifically to promote the measurement of the optical characteristic but to suppress other components that contribute to the signal. When using a luminescent sensor material, for example, the sensor filter may comprise a bandpass filter and/or an edge filter, which is designed and arranged to transmit luminescence light from the sensor material (that is to say to pass at least part of it through, preferably with a transmission of greater than 50%), while in contrast light at a wavelength outside the wavelength range of the luminescence (that is to say outside a predetermined wavelength range around the maximum of the luminescence) is at least partially suppressed (that is to say for example is transmitted with a transmission of less than 50%). In principle, the same filter techniques can be used in this case as for the background filter already described above. This development of the invention has the advantage that the signal quality (for example the signal-to-noise ratio) is further improved since all that is measured is that component of the light which has an information content relating to the analyte.

Further advantageous refinements relate to the use of reference detectors and/or background detectors. For example, a reference device may be provided, with the ocular sensor furthermore comprising a reference material. By way of example, the reference material may once again be introduced into the ocular sensor as a separate layer, for example in the form of a layer which is applied to the sensor chip, or the reference material may be implemented in a carrier material. The above statements relating to the sensor material apply analogously to the options for implementation in the carrier material.

In this case, the reference material should be designed such that it changes at least one optical characteristic, in particular once again luminescence (for example fluorescence or phosphorescence) as a function of the intensity of the excitation light. However, in contrast to the sensor material, this reference material is not designed such that this change in the at least one optical characteristic, for example once again the fluorescence behaviour, is at least substantially independent of the presence and/or absence of the at least one analyte to be verified. For example, the reference material may be designed such that its relative fluorescence change in the presence of the analyte is negligibly small in comparison to the relative fluorescence change of the sensor material, for example in the range $<\frac{1}{10}$, $<\frac{1}{100}$ or even less for a ratio of the relative fluorescence changes. By way of example, this reference material may once again be a material which can be excited to fluoresce, but whose fluorescence is not substantially influenced by the analyte.

In this case, the ocular sensor may also comprise at least one optical reference detector, for example once again a photodiode. Once again, this optical reference detector can preferably be integrated in the sensor chip, in which case the statements made above with regard to the optical detector apply analogously. This optical reference detector should be designed to measure the optical characteristic of the reference material, for example the analyte-independent fluorescence of the reference material.

In order to improve the reference signal generated by this optical reference detector and to at least largely remove interference components from it, it is also possible to provide at least one reference filter. Once again, for example, this may be a bandpass filter and/or an edge filter. This filter should be designed such that the luminescence of the reference material is at least largely transmitted (that is to say preferably with a transmission of more than 50%), and can therefore arrive at the reference detector. Light at a wavelength outside the wavelength range of the reference luminescence (that is to say outside a range which is predetermined around the reference luminescence maximum) should in this case be suppressed. This ensures that the reference detector generates, at least substantially, a reference signal which is dependent only on the excitation intensity of the excitation light. This reference signal can be used for evaluation of the signal from the optical detector, for example by relating the two signals to one another in order in this way, for example, to make it possible to calculate an analyte concentration in the eye fluid. Alternatively, however, it is also possible to use more complex evaluation algorithms.

Alternatively or in addition to the use of a reference detector, it is also possible to provide an optical background detector. For example, this may once again be a photodiode integrated in the chip, in which case the above statements apply analogously. This background detector should be designed to measure an intensity of the excitation light. This excitation light may preferably be the actual excitation light used to excite the sensor material and/or the reference material, that is to say for example environmental light which has already been filtered by the background filter (for example daylight). This background signal can also once again be used to determine a concentration of the analyte, for example once again by forming a ratio of the signal from the optical detector and the background signal. More complex evaluation algorithms are, however, also once again feasible, for example the use of the excitation light, in order to eliminate a background signal.

In addition to the refinements described above, further advantageous developments of the ocular sensor are feasible. For example, a geometric structure may be provided which has a light trap. By way of example, this light trap may be designed to suppress direct transmission of excitation light, in particular of unfiltered environmental light, to the optical detector while in contrast allowing diffusion of sensor material, for example excited sensor modules, and/or diffusion of the analyte to the optical detector. This makes it possible to further improve the signal quality.

Further advantageous refinements of the invention relate to the manner of reading the information which can be generated by means of the ocular sensor. For example, the ocular sensor advantageously also has at least one interface for interchanging information with an evaluation unit.

This interface may be designed in many different ways. For example, the sensor chip may have a data memory in which information generated by the ocular sensor can be stored and can be called up. For example, the ocular sensor may be in the form of an eye lens which, after removal from the eye (this may, for example, be a disposable lens) is inserted into a corresponding reader in which (for example by appropriate electrical contacts) contact is made, for example, to specific contact pads on the sensor chip, in order to check stored information.

Alternative or additionally, however, the at least one interface may also comprise an interface for wire-free data transmission. In this case, in particular, infrared and/or radio-frequency techniques may be used which, for example, are known from transponder technology. This development has the advantage that information can be checked "on-line" during measurement or shortly after this measurement and can then be conveyed, for example, to the patient, to a doctor or to a further appliance, for example to a computer or a medication appliance. Wire-free interfaces such as these can also be implemented using the available ASIC technologies.

It has been found to be particularly advantageous to use a system in which the ocular sensor has a capacitive element. The evaluation unit can be used for coupling to this capacitive element which, for example, may comprise a single plate of a capacitor, thus allowing information to be interchanged without any need to make a physical contact between the evaluation unit and the ocular sensor. This allows data to be interchanged conveniently and safely with contact lenses located in the eye, and/or with implants.

By way of example, the interface may in this case be designed such that the capacitive element forms a resonant circuit together with a resistance element and/or an inductive element, which resonant circuit can be excited by the evaluation unit. In this case, the optical detector can preferably be connected in parallel with the resistance element and/or the optical detector. Alternatively or additionally, any reference detectors and/or background detectors which may be present can also be connected in an appropriate manner. If one of these detectors responds, then the characteristics of the resonant circuit therefore change, in particular, for example, a frequency of the resonant circuit. This frequency change, which is therefore dependent on the generated signal (detector signal, reference signal, background signal), can be detected by the evaluation unit.

Various refinements are feasible in this case. For example, an appropriate resonant circuit can be provided for each of the detectors, with each of these resonant circuits preferably having a different resonant frequency. This makes it possible, for example, for the evaluation unit to check all of the detectors at the same time or else with a time offset. Alternatively, however, preprocessing can also be carried out on the sensor chip itself, for example by appropriate quotient formation or the like, as a result of which a cleaned overall signal and/or a preprocessed signal is read at this stage by means of the evaluation unit.

Accordingly, in addition to the ocular sensor, a measurement system for verification of the at least one analyte in the eye fluid is proposed in one of the refinements described above, which comprises an ocular sensor according to one of the refinements described above, furthermore as well as at least one evaluation unit which is designed to interchange information with the sensor chip.

This evaluation unit can preferably be in the form of an evaluation unit which is physically separate from the ocular sensor, and is preferably in the form of a portable appliance. For example, in this case, this may be a handheld appliance, with an edge length of preferably no more than 15 cm, preferably of less than 10 cm, which can be carried conveniently by a patient in a pocket or on the belt.

For example, in the case of the described refinement of the interface of the ocular sensor with a capacitive element, the evaluation unit may be equipped with an excitation unit which, together with the interface of the sensor chip, forms an excited resonant circuit. This principle has the advantage that, in principle, the sensor chip does not need its own energy source (although, of course, this may actually be the case), thus making it possible, in particular, to greatly increase the useful life of implanted ocular sensors. The excitation unit may comprise an oscillation generator whose energy is transmitted inductively to the capacitive element of the interface of the ocular sensor. In practice, systems such as these have been found to be excellently suitable for transmission ranges of up to about 1 m, which means that the evaluation unit for reading the sensor chip can even be carried in a pocket, and need not be kept in front of the eye. This makes it possible, for example, to carry out automated measurements without any user action being required by the patient. Measurement systems such as these are therefore particularly user-friendly, particularly for elderly patients, children and handicapped patients, in which case it is possible to greatly reduce the risk of incorrect control actions, by means of automated program procedures. It is also feasible for measurement systems such these to interact with automatic medication systems, for example insulin pumps.

In addition, by way of example, the evaluation unit may contain interfaces for interaction with a user, for example a keypad, interfaces for a computer, a display or the like. Furthermore, the evaluation unit may itself comprise a computer, for example a microcomputer, which can be programmed appropriately. Appropriate data memories of a volatile and/or non-volatile type can also be provided.

By way of example, the evaluation unit can be programmed such that it determines a concentration of the at least one analyte in the eye fluid using the signals or measurement results produced by the ocular sensor. By way of example, this result can be stored in a data memory or can be output to the patient and/or via an interface to a doctor or a database.

However, in many cases, the concentration of the at least one analyte in the eye fluid is of less interest. In fact, frequently, concentrations in other bodily fluids are quoted, for example concentrations in the blood and/or urine. By way of example, glucose is normally quoted as blood glucose. The evaluation unit can accordingly also be designed to calculate a concentration of the at least one analyte in a further bodily fluid, for example in blood and to output this in an appropriate manner (see above), and/or to store it, for example by means of an appropriate computer with appropriate software. For this purpose, the evaluation unit may, for example, have reference tables which convert a concentration of the analyte in the eye fluid to concentrations in other fluids. Alternatively or additionally, conversion algorithms or conversion curves may also be used.

Furthermore, it has been found that the accuracy of the results can be greatly increased by the measurement system additionally having a calibration system. This calibration system can be used, for example, to improve the evaluation of the signals from the sensor chip, that is to say to make the calculation of the concentration of the analyte in the eye fluid and/or the further bodily fluid independent of natural scatters, for example discrepancies from one patient to another relating to the physiological constraints. Discrepancies relating to the positioning of the ocular sensor in the eye, production tolerances of the ocular sensor, or the like.

This calibration system can accordingly be designed to receive and/or to process at least one calibration information item relating to a concentration of the analyte in the eye fluid and/or a further bodily fluid, and accordingly to carry out a calibration of the determination of the analyte concentration. For example, the calibration system can for this purpose receive, via an interface, external data relating to an analyte concentration in the eye fluid and/or the further bodily fluid, which has been obtained by a separate measurement system. Alternatively or additionally, the calibration system can also itself have at least one instrument for determining the concentration of the analyte. Conventional instruments, for example instruments which determine the analyte concentration by means of a test element, are particularly preferred in this case. In this case, by way of example, electrochemical test strips and/or optical test strip systems are used, such as those which a person skilled in the art will be familiar with, for example, from the field of blood glucose determination.

In this case, by way of example, the measurement system may be designed such that a calibration measurement such as this is carried out before the measurement system is started up, in order to match the data produced by the ocular sensor with the data from the "conventional" instrument. Furthermore, alternatively or additionally, it is also possible to carry out a calibration measurement at regular intervals in which case, for example, the measurement system can be designed such that the system itself indicates to a user the need for a calibration measurement such as this at specific time intervals (for example once a day, in comparison to up to seven times a day as required for "conventional" measurements). Automatic calibration measurements are also possible, for example calibration measurements by means of a further implanted sensor.

Overall, this refinement of the measurement system using a calibration system results in a further improvement in the measurement accuracy, and therefore in an improvement in the reliability of the physiological information obtained about the patient.

EXEMPLARY EMBODIMENTS

Further details and features of the invention will become evident from the following description of preferred exemplary embodiments in conjunction with the dependent claims. In this case, the respective features may be implemented on their own or in groups of more than one, in combination with one another. The invention is not restricted to the exemplary embodiments. The exemplary embodiments are illustrated schematically in the figures. The same reference numbers in the individual figures in this case denote identical or functionally identical elements, or elements whose functions correspond to one another.

In detail:

Figure 1:
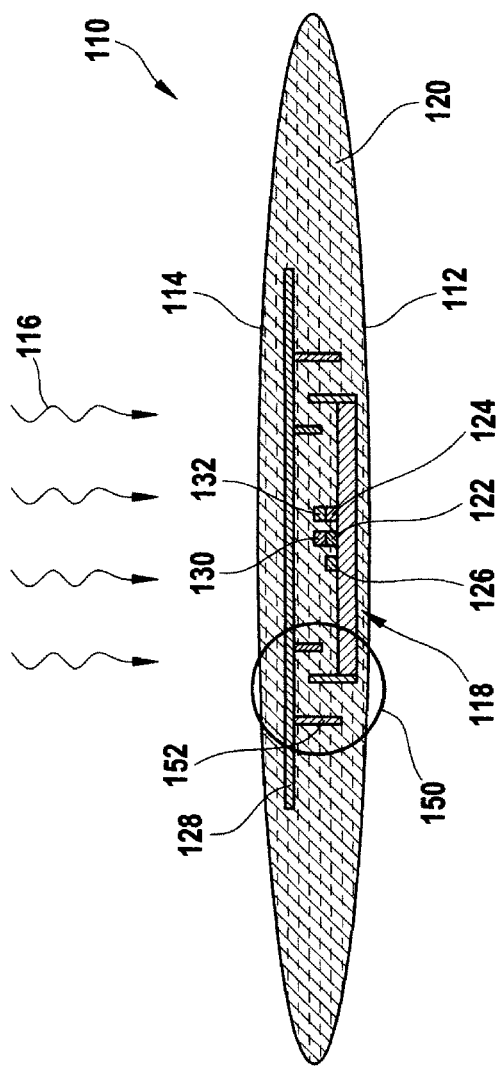
FIG. 1 shows a schematic illustration of an ocular sensor.

FIG. 1 illustrates, in a highly schematic form, one exemplary embodiment of an ocular sensor 110 according to the invention. In this case, by way of example, the ocular sensor is in the form of an implant and may, for example, be implanted in or under a conjunctiva of a patient. The ocular sensor 110 has an eye side 112 and an outside 114. Daylight 116 can accordingly strike the ocular sensor 110 from the outside 114.

The ocular sensor 110 has a sensor chip 118 which, as described above, is preferably in the form of an ASIC. This sensor chip 118 is embedded in a bio-compatible hydrogel as a carrier material 120. This carrier material therefore provides the ocular sensor 110 with the necessary mechanical robustness, but is at the same time deformable and flexible, in order to match itself to the eye, and allows diffusion of the analyte.

In this exemplary embodiment, a sensor material is mixed into the carrier material 120. For example, this sensor material may comprise sensor materials for verification of glucose in an eye fluid, for example in tear fluid, aqueous humour or interstitial eye fluid. Examples of sensor materials such as these are described in WO 01/13783 A1, WO 02/087429 A1 and WO 2004/071287 A1. In the present exemplary embodiment, the following sensor materials are particularly preferably used: Concanavalin A/dextran, glucose-galactose binding protein (GGBP), Glucose-hexokinase boric acid ester (as described, for example, in PCT/EP2004/008825). However, other sensor materials can also be used, as well as mixtures or combinations of a plurality of sensor materials. This sensor material can be distributed homogeneously directly in the hydrogel, but can also be enclosed in microcapsules which themselves are once again preferably distributed in the hydrogel.

Normally, an implanted ocular sensor 110 such as this, as described by way of example in WO 01/13783 A1, is excited to fluoresce from the exterior, that is to say from the outside 114, by a suitable light source (for example a light-emitting diode with a bandpass filter and/or a laser diode), and the fluorescence at one or more wavelengths is measured by means of a suitable photometer. The intensity of the fluorescence signal is in this case, of course, dependent, however, not only on the analyte concentration but also on the distance and angle between the implant and the photometer, and/or the excitation light source.

As described above, the present ocular sensor 110 solves this problem in that it contains the sensor chip 118 as an integral component. This sensor chip 118, which is preferably in the form of an ASIC, may, for example, be manufactured on a customer-specific basis and, for example, may be based on organic or inorganic semiconductor material, for example silicon. In this case, at least a portion of the evaluation and drive electronics can be integrated on the sensor chip 118.

In this exemplary embodiment, the sensor chip 118 comprises three photodiodes: in addition to the actual measurement diode 122 as an optical detector, a reference diode 124 and a background diode 126 are integrated on the sensor chip 118. The necessary drive circuits and evaluation circuits are likewise integrated on the sensor chip 118, but these are not illustrated in FIG. 1.

In addition to the sensor material, a reference material is also mixed into the carrier material 120, for example a reference fluorophor, whose luminescence can likewise be excited by the daylight 116, but with this reference fluorescence being independent of the presence of the analyte to be verified.

Figure 2:
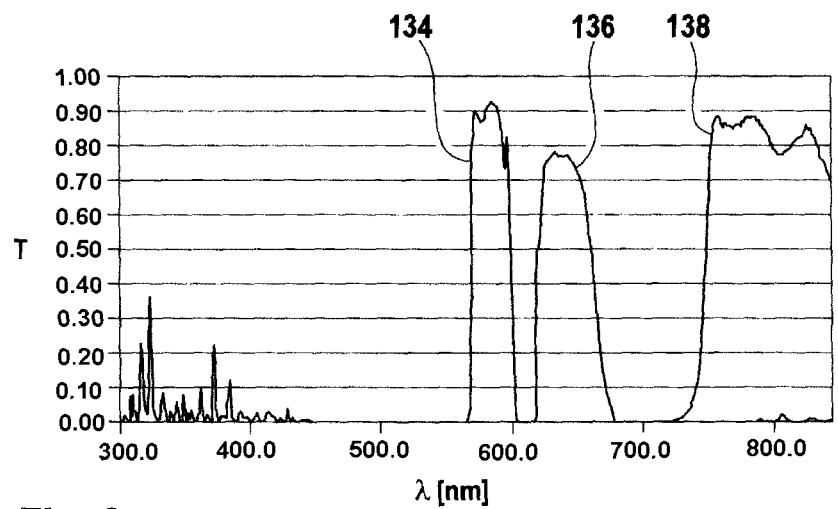
FIG. 2 shows an illustration of the filter characteristics of the filter used in the ocular sensor shown in FIG. 1.

In order to allow the various light components to be recorded separately by means of the three diodes 122, 124, 126, various filters are also provided. The sensor chip 118 is therefore first of all covered by a background filter 128. This background filter 128 in this exemplary embodiment is in the form of an interference filter. The measurement diode 122 is also covered by a sensor filter 130 and the reference diode 124 by a reference filter 132. The sensor filter 130 and the reference filter 132 are also preferably in the form of interference filters. The background diode 126 is no longer equipped with a filter (except by means of the background filter 128). The transmission characteristics of these filters 128, 130 and 132 are shown in FIG. 2. FIG. 2 shows the transmission spectra (the figure in each case shows a normalized transmission T plotted against the wavelength λ) of these filters 128, 130, 132. In this case, the curve 134 shows the transmission of the background filter 128, the curve 136 the transmission of the sensor filter 130, and the curve 138 the transmission of the reference filter 132. As can be seen, the filters 128 and 130 are in the form of bandpass filters, having a transmission from about 560 to 600 nm, and about 620 to 670 nm, respectively. In contrast, the reference filter 132 is essentially in the form of an edge filter and "opens" above a wavelength of about 740 nm.

The spectral characteristics of the three filters 128, 130 and 132 are in this case designed such that the filter 128 has transmission in the region of the excitation wavelength of the sensor material. The filters 130 and 132, in contrast, have transmission in the region of the luminescence wavelength of the sensor material (sensor filter 130) and, respectively, in the region of the fluorescence of the reference material (reference filter 132).

The ocular sensor 110, which is in the form of an implant is, according to the invention, implanted under the conjunctiva of the eye, where it is subject to normal daylight 116. Since the conjunctiva is highly transparent, in contrast to normally pigmented skin, a comparatively high proportion of the light enters the ocular sensor 110, which is in the form of an implant.

Figure 3:
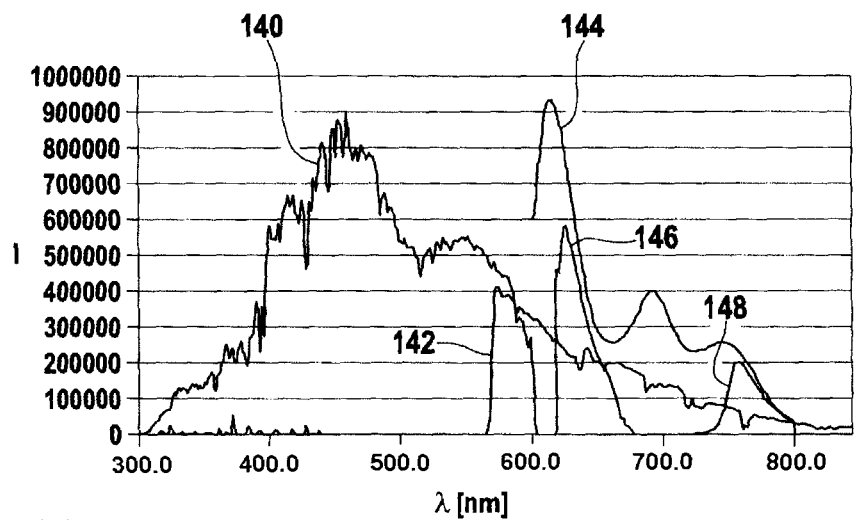
FIG. 3 shows a spectral representation of the light conditions in the ocular sensor shown in FIG. 1.

FIG. 3 shows the spectral light conditions that occur in the ocular sensor 110 (the intensity I is plotted against the wavelength λ in the figure). In this case, the curve 140 shows the intensity distribution of the daylight 116.

Since the sensor chip 118 is completely surrounded by the background filter 128 (cf. the transmission characteristic 134 in FIG. 2), only that component of the daylight 116 which is required for excitation of the sensor material passes through. The spectral intensity distribution of this actual excitation light is shown by the curve 142 in FIG. 3, and is obtained by multiplication of the curve 134 in FIG. 2 by the intensity distribution of the daylight 140 in FIG. 3. This intensity 142 of the excitation light is measured by means of the background diode 126 (see FIG. 1) on the sensor chip 118.

This excitation light 142 excites not only the fluorescence of the sensor material (fluorescence analyte-dependent) but also the fluorescence of the reference material (fluorescence analyte-independent). This excitation therefore results in an overall fluorescence 144, which is composed of these two fluorescence components.

In order to separate these fluorescence components, the measurement diode 122 is used with the sensor filter 130 and the reference diode 124 is used with the reference filter 132 (cf. FIG. 1). In a corresponding manner, the overall fluorescence 144 in FIG. 3 can once again be multiplied by the transmission curves 136 and 138 as shown in FIG. 2. This filtering therefore leads to a sensor fluorescence 146 which is detected by the measurement diode 122, and to a reference fluorescence 148 which is detected by the reference diode 124. In this way, the background diode 146 provides information on the intensity with which the sensor material and the reference material are excited, the measurement diode 122 provides information about the analyte-dependent sensor fluorescence of the sensor material, and the reference diode 124 provides analyte-independent information about the reference fluorescence of the reference material. The concentration of the analyte in the eye fluid can be deduced with high accuracy from these three signal components.

Since there is a fixed relationship between the three photodiodes 122, 124 and 126 and the sensor material and the reference material, the measurement signal or the measurement signals is or are no longer position-dependent. Ideally, the measurement signal is therefore dependent only on the excitation energy (this information is obtained by the background diode 126) and the analyte concentration. The simultaneous provision of information from the background diode 126 and from the reference diode 124 is, to a certain extent, redundant, but the additional information increases the robustness and measurement accuracy of the system. For example, particularly when the reference material and the sensor material have similar spectral excitation characteristics, changes in the spectral characteristic of this excitation light can be compensated for, for example the change from daylight to artificial environmental light. This considerably improves the flexibility of application, thus allowing measurements of the analyte concentration to be carried out at different times of day and/or when there is a change in the light conditions (daylight, artificial light).

The arrangement of the ocular sensor 110 as shown in FIG. 1 has a further special feature in the form of a light trap 150. This light trap 150 takes account of the fact that, on the one hand, the three photodiodes 122, 124 and 126 on the sensor chip 118 are intended to be completely surrounded by the background filter 128, since any daylight 116 which otherwise enters would lead to an offset which in general would be considerably greater than the actual measurement signal. On the other hand, the sensor material is intended to be accommodated within the ocular sensor 110, and free diffusion of the analyte should be possible. This problem is solved in the described exemplary embodiment by the light trap 150, which allows diffusion of the analyte in the carrier material 120 but suppresses the ingress of unfiltered daylight 116. Typically, as is shown in FIG. 1, mechanical light traps 150 are provided by a plurality of intersecting webs 152. Other types of light traps 150, for example optical "labyrinths" can also be used, for example as known from smoke-alarm technology.

A further option, which can be used alternatively or additionally, is to mark the hydrogel of the carrier material 120 itself with appropriate dye molecules, as a result of which the background filter 128 is not in the form of an interference filter but in the form of a bulk filter. This also makes it possible to provide the transmission 134 approximately. However, typical filter characteristics of such dye molecules are broader than the filter characteristics of the curve 134 shown in FIG. 2. Furthermore, the advantage of an interference filter is that the spectral characteristic can be influenced comparatively easily. For example, interference filters could be produced by deposition of a thin metal layer sequence and/or metal-compound layer sequence on a transparent guide, for example a thin glass and/or a plastic material, with this then being implemented in the ocular sensor 110, and/or placed on the sensor chip 118, as shown in FIG. 1. However, it is also possible to apply the filter directly to the sensor chip 118, for example as a consequence of one or more vapour-deposition layers, and, in addition, to implement mechanical light traps 150 in the form of MEMS (micro electro-mechanical systems) on the sensor chip 118.

Figure 4:
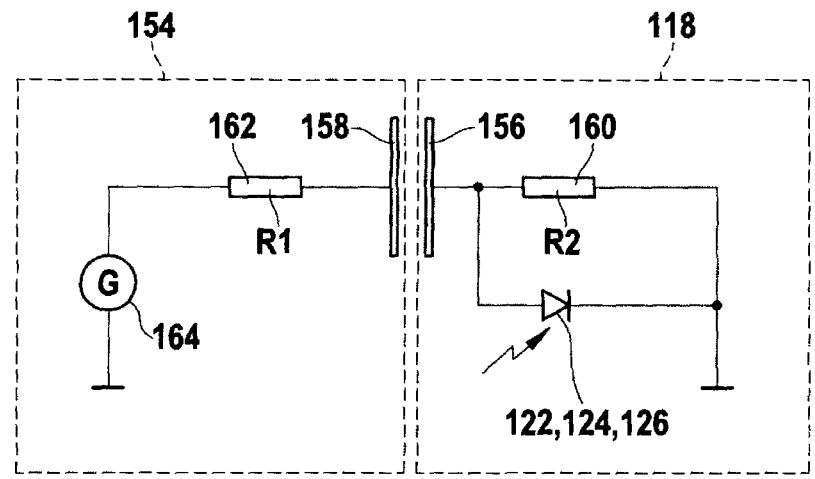
FIG. 4 shows a schematic illustration of the interaction of an excitation unit of an evaluation unit with an interface of the ocular sensor.

FIG. 4 shows, highly schematically, one option for reading the sensor chip 118. The sensor chip 118, which in this case is shown only incompletely in FIG. 4, in this case interacts with an excitation unit 154 which is implemented in an evaluation unit (cf. FIG. 5). In this case, capacitive elements 156 and 158, respectively, are used as an interface between the sensor chip 118 and the excitation unit 154, and these are illustrated schematically as individual capacitor plates in FIG. 4. In this case, the capacitive element 156 of the sensor chip 118 is connected via a resistor 160 to earth (for example a relatively large metal surface on the sensor chip 118). The diodes 122, 124 and 126 are connected in parallel with the resistor 160. As stated above, the circuit can be designed such that these diodes are switched individually or are all switched in the manner illustrated in FIG. 4.

In the excitation unit 154, the capacitive element 158 is connected via a resistor 162 to a generator 164, which is in turn connected at its other connection to earth. The excitation unit 154 and the sensor chip 118 in this circuitry form an excited electrical resonant circuit. The generator 164 produces a changing electrical field at the capacitive elements 156, 158. The natural frequency of the resonant circuit is governed by the capacitances (governed by the interaction of the capacitive elements 156, 158) and the resistors 160, 162 in the resonant circuit. The total resistance of the parallel circuit comprising the resistor 160 and the diodes 122, 124, 126, and therefore the natural frequency of the resonant circuit, are changed by shining light on the diodes 122, 124, 126. By way of example, this change can be measured and evaluated as a field strength change. The excitation unit 154 may accordingly comprise a field needle and a field strength measurement apparatus, in order to measure these field strength changes. However, alternatively or additionally, other measurement techniques may also be used, for example measurement of the power output of the generator 164.

Figure 5:
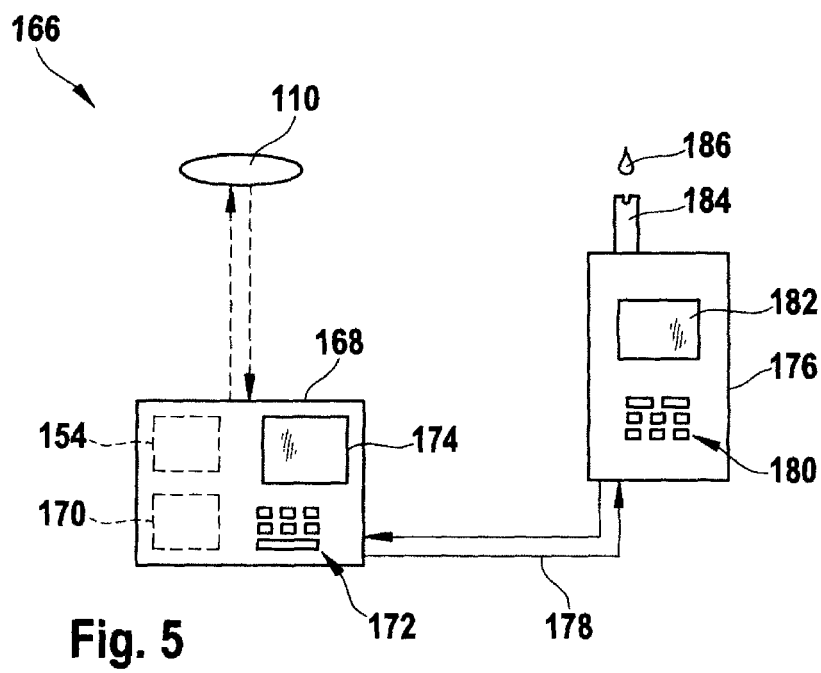
FIG. 5 shows one exemplary embodiment of a measurement system having an ocular sensor, an evaluation unit and a calibration system.

In FIG. 5 shows, highly schematically, a measurement system 166 for verification of the at least one analyte in an eye fluid. The measurement system 166 comprises an ocular sensor 110, for example an ocular sensor in the form described in FIG. 1, which, for example, may be in the form of an implant and/or an eye lens. The measurement system 166 furthermore comprises an evaluation unit 168 with an excitation unit 154 (for example as shown in the exemplary embodiment in FIG. 4) and a microcomputer 170. By way of example, the evaluation unit 168 can interchange information with the ocular sensor 110 and/or with the sensor chip 118 by means of the process described in FIG. 4, and can thus check measurement data "in situ" (that is to say without having to remove the ocular sensor 110 from the eye fluid). In this case, the evaluation unit 168 may be kept at any desired point on the patient's body. The body can then be used as part of the interface, in addition to the capacitive elements 156, 158 shown in FIG. 4, and contributes to the data transmission.

The microcomputer 170 of the evaluation unit 168 is preferably designed in accordance with the above description and is used to control the measurement and to evaluate the measurement results. The microcomputer 170 can be controlled by a user by means of control elements 172, and can output information to a user via a display 174. However, other user interfaces can also be implemented.

Furthermore, as shown in the exemplary embodiment in FIG. 5, the measurement system 166 comprises a calibration system 176. This calibration system 176 is preferably implemented in the evaluation unit 168. In the schematic exemplary embodiment illustrated in FIG. 5, the calibration unit 176 is, however, in the form of a separate unit, which communicates with the evaluation unit 168 via an interface 178. This may be a wire-free and/or a wire-based interface or else data interchange apparatuses may be provided by means of data storage media (for example memory chips) which are interchanged between the calibration system 176 and the evaluation unit 168 manually by the patient, as "interfaces" for connection of these elements.

The calibration system 176 also has control elements 180, a display 182 and (not illustrated in FIG. 5) appropriate electronics, for example once again a microcomputer and/or other electronic components. The calibration system 176 is in this case designed to use a test strip 184 to verify the concentration of the analyte in a bodily fluid, and this is illustrated symbolically as blood droplet 186. Conventional, commercially available instruments, such as blood glucose meters, can therefore be used as the calibration system 176. Systems such as these normally have appropriate interfaces as well, such as infrared interfaces. The information obtained by means of the calibration system 176 relating to the analyte concentration in the bodily fluid, for example the blood glucose concentration, can be communicated via the interface 178 to the evaluation unit 168 in order to be used there for matching with the information of the sensor chip 118 of the ocular sensor 110. The measurement result of the blood glucose measurement can therefore be entered directly in the algorithm for indirect blood glucose determination with the ocular sensor 110.

| List of reference symbols | |
|---|---|
| 110 | Ocular sensor |
| 112 | Eye side |
| 114 | Outside |
| 116 | Daylight |
| 118 | Sensor chip |
| 120 | Carrier material |
| 122 | Measurement diode |
| 124 | Reference diode |
| 126 | Background diode |
| 128 | Background filter |
| 130 | Sensor filter |
| 132 | Reference filter |
| 134 | Background filter transmission |
| 136 | Sensor filter transmission |
| 138 | Reference filter transmission |
| 140 | Daylight intensity |
| 142 | Excitation light intensity |
| 144 | Overall fluorescence |
| 146 | Sensor fluorescence |
| 148 | Reference fluorescence |
| 150 | Light trap |
| 152 | Webs |
| 154 | Excitation unit |
| 156 | Capacitive element |
| 158 | Capacitive element |
| 160 | Resistor |
| 162 | Resistor |
| 164 | Generator |
| 166 | Measurement system |
| 168 | Evaluation unit |
| 170 | Microcomputer |
| 172 | Control elements |
| 174 | Display |
| 176 | Calibration system |
| 178 | Interface |
| 180 | Control elements |
| 182 | Display |
| 184 | Test strip |
| 186 | Blood droplet |

The invention claimed is:

1. An ocular sensor for verification of at least one analyte in an eye fluid, with the ocular sensor having at least one sensor material, with the sensor material being designed to change at least one optical characteristic in the presence of the at least one analyte, with the ocular sensor also having at least one sensor chip, with the sensor chip having at least one integrated optical detector for verification of the optical characteristic, with the ocular sensor having a carrier material, with the sensor chip being embedded in the carrier material and with the sensor chip being in direct contact with the carrier material, and with the sensor material being entirely or partially contained in the carrier material, with the carrier material comprising a material which is at least partially permeable for the analyte, and with the sensor material being contained in the carrier material in at least one of the following manners: the sensor material is mixed into the carrier material; the sensor material is dissolved in the carrier material; the sensor material is entirely or partially a component of the carrier material; and the sensor material is implemented in microcapsules.

2. The ocular sensor according to claim 1, with the ocular sensor comprising at least one of the following elements: an eye lens, a contact lens, an inlay, and an eye implant.

3. The ocular sensor according to claim 1, with the carrier material having at least one of the following characteristics:
the carrier material comprises a deformable material;
the sensor material is entirely or partially mixed into the carrier material;
the sensor material is entirely or partially embedded in microcapsules which are dispersed in the carrier material;
the sensor material is entirely or partially dissolved in the carrier material; and
the sensor material is entirely or partially a component of the carrier material.

4. The ocular sensor according to claim 1, with the optical detector comprising at least one photoelectric element.

5. The ocular sensor according to one claim 1, with the at least one optical characteristic comprising luminescence which can be excited by excitation light.

6. The ocular sensor according to claim 5, with the ocular sensor being designed to allow excitation of the sensor material by an excitation light source.

7. The ocular sensor according to claim 6, with the ocular sensor having at least one of the following designs:
the ocular sensor is designed to allow external excitation light access to the sensor material, and
the sensor chip has an integrated excitation light source.

8. The ocular sensor according to claim 7, wherein the integrated excitation light source is an integrated light-emitting diode and/or a laser diode.

9. The ocular sensor according to claim 5, with the ocular sensor also having an optical background filter, which is designed and arranged to entirely or partially filter the light from the excitation light source.

10. The ocular sensor according to claim 9, with the background filter having at least one of the following designs:
the background filter is in the form of a separate background filter; and
the background filter is entirely or partially in the form of a component of the carrier material.

11. The ocular sensor according to claim 9, wherein the optical background filter is an optical bandpass filter or edge filter.

12. The ocular sensor according to claim 5, with the ocular sensor also having a sensor filter, which is designed and arranged to transmit luminescence light of the sensor material and to at least partially suppress light outside the wavelength range of the luminescence light.

13. The ocular sensor according to claim 5, with the ocular sensor furthermore having a reference material, with the reference material being designed to change at least one optical characteristic, as a function of the intensity of the excitation light and independently of the presence of the analyte.

14. The ocular sensor according to claim 13, with the sensor chip furthermore having an optical reference detector which is designed to measure the optical characteristic of the reference material.

15. The ocular sensor according to claim 14, with the ocular sensor furthermore having a reference filter, with the optical characteristic of the reference material being a reference luminescence and with the reference filter being designed and installed to allow transmission of the reference luminescence to the reference detector and to suppress transmission of light at a wavelength outside the wavelength range of the reference luminescence.

16. The ocular sensor according to claim 13, wherein the reference material is designed to change fluorescence or phosphorescence.

17. The ocular sensor according to claim 5, with the ocular sensor furthermore having an optical background detector which is designed to measure an intensity of the excitation light.

18. The ocular sensor according to claim 5, with the ocular sensor furthermore having a light trap, with the light trap being designed to suppress transmission of light from the excitation light source to the optical detector, and with the light trap being designed to allow diffusion of the sensor material and/or of the analyte to the optical detector.

19. The ocular sensor according to claim 5, wherein the luminescence is fluorescence or phosphorescence.

20. The ocular sensor according to claim 1, with the ocular sensor furthermore having an interface for interchanging information with an evaluation unit.

21. The ocular sensor according to claim 20, with the interface having at least one interface for wire-free data transmission.

22. The ocular sensor according to claim 21, with the interface having at least one capacitive element.

23. The ocular sensor according to claim 22, with the interface furthermore having at least one resistance element, which is connected in parallel with the optical detector and/or the reference detector and/or the background detector, and/or having an inductive element which is connected in parallel with the optical detector and/or the reference detector and/or the background detector.

24. A measurement system for verification of at least one analyte in an eye fluid, comprising an ocular sensor according to claim 1, furthermore also comprising an evaluation unit which is designed to interchange information with the sensor chip.

25. The measurement system according to claim 24, with the evaluation unit comprising an excitation unit which is designed to form a resonant circuit with an interface of the sensor chip.

26. The measurement system according to claim 25, with the resonant circuit being designed to change at least one electrical characteristic, as a function of the signal from the optical detector and/or from the reference detector and/or from the background detector.

27. The measurement system according to claim 24, with the evaluation unit being designed to determine the concentration of the analyte in the eye fluid.

28. The measurement system according to claim 27, with the evaluation unit also being designed to determine a concentration of the at least one analyte in a further bodily fluid.

29. The measurement system according to claim 24, furthermore comprising a calibration system which is designed to process at least one calibration information item relating to a concentration of the analyte in the eye fluid and/or a further bodily fluid, and to carry out a calibration of the determination of the analyte concentration in the eye fluid and/or the further bodily fluid.

30. The measurement system according to claim 29, with the calibration system having at least one instrument for determination of the concentration of the analyte comprising a test element.

31. The ocular sensor according to claim 1, wherein the carrier material comprises a hydrogel.

32. The ocular sensor according to claim 1, wherein the sensor material comprises functional groups which are bound to a matrix material of the carrier material.

* * * * *